US005792604A

United States Patent [19]
Jefferies et al.

[11] Patent Number: 5,792,604
[45] Date of Patent: Aug. 11, 1998

[54] METHOD OF IDENTIFYING MHC-CLASS I RESTRICTED ANTIGENS ENDOGENOUSLY PROCESSED BY CELLULAR SECRETORY PATHWAY

[75] Inventors: Wilfred A. Jefferies, South Surrey; Reinhard Gabathuler; Gerassimos Kolaitis, both of Vancouver; Gregor S. D. Reid, Vancouver, all of Canada

[73] Assignee: University of British Columbia, Vancouver, Canada

[21] Appl. No.: 614,142

[22] Filed: Mar. 12, 1996

[51] Int. Cl.$^6$ .................. G01N 33/53; G01N 33/569
[52] U.S. Cl. .................. 435/5; 435/6; 435/7.21; 435/7.22; 435/7.23; 435/7.24; 435/7.32
[58] Field of Search .................. 435/5, 6, 7.21, 435/7.22, 7.23, 7.24, 7.32

[56] References Cited

FOREIGN PATENT DOCUMENTS

| | | |
|---|---|---|
| WO92/04033 | 3/1992 | WIPO . |
| WO92/11289 | 7/1992 | WIPO . |
| WO93/00304 | 1/1993 | WIPO . |
| WO93/02690 | 2/1993 | WIPO . |

OTHER PUBLICATIONS van Bleek and Nathanson, Nature, 348:213, 1990.
Zhang et al., Proc. Natl. Acad. Sci. USA, 89:8403, 1992.
Matsumura et al., Science, 257:927, 1992.
Latron et al., Science, 257:964, 1992.
Nuchtern et al., Nature, 339:223, 1989.
Yewdell and Bennink, Science, 244:1072, 1989.
Cox et al., Science, 247:715, 1990.
Deverson et al., Nature, 348:738, 1990.
Trowsdale et al, Nature, 348:741, 1990.
Spies et al., Nature, 348:744, 1990.
Monaco et al., Science, 250:1723, 1990.
Spies and DeMars, Nature, 351:323, 1991.
Bahram et a l., Proc. Natl. Acad. Sci. USA, 88:10094, 1991.
Spies et al., Nature, 355:644, 1992.
Kelly et al., Nature, 355:641, 1992.
Powis et al., Proc. Natl. Acad. Sci. USA, 89:1463, 1992.
Colonna et al., Proc. Natl. Acad. Sci. USA, 89:3932, 1992.
Monaco and McDevitt, Proc. Natl.Acad. Sci. USA, 79:3001, 1982.
Ortiz–Navarette et al.,Nature, 353:662, 1991.
Brown et al., Nature 353:355, 1991.
Glynne et al., Nature 353:357, 1991.
Martinez and Monaco, Nature, 353:664, 1991.
Kelly et al., Nature, 353:667, 1991.
Yang et al., Proc. Natl. Acad. Sci. USA, 89:4928, 1992.
Goldberg and Rock, Nature, 357:375, 1992.
Falk et al., Nature, 348:248, 1990.
Rötzschke et al., Nature, 348:252, 1990.
Arnold et al., J. Exp. Med., 182:885, 1995.
Udono and Srivastava, J.Exp. Med., 178:1391, 1993.
Udono and Srivastava, J. Immunol., 152:5398, 1994.
Huang et al., Science, 264:961, 1994.
Sinha et al., Science, 248:1380, 1990.
Rammensee et al., Immunogenetics, 41:178, 1995.
Restifo et al., J. Exp. Med., 177:265,1993.
Williams et al., J. Immunol., 142:2796, 1989.
Rock et al., J. Immunol. 150:1244, 1993.
Moss, Seminars in Immunol. 2:317, 1990.
Ossevoort et al., Eur. J. Immunol. 23:3082, 1993.
Jefferies et al., J. Immunol., 151:2974, 1993.
Townsend et al., Nature, 340:443–448, 1989.
Yang et al., J. Biol. Chem., 267:11669–11672, 1992.
Driscoll et al., Nature, 365:262, 1993.
Hunt et al., Science, 255:1261–1263, 1992.
Henderson et al., Science, 25:1264–1266, 1992.
Moskophidis et al., nature 362:758–761, 1993.
Bevan, M.J., J. Exp. Med., 143:1283–1288, 1976.
Kärre et al., Nature, 319:675–678, 1986.
Falk et al., Cell. Immunol., 150:447–452, 1993.
Rotam–Yehudar eta l., J. Exp. Med., 180:477–488, 1994.
Brown et al., J. Immunol., 151:1193–1204, 1993.
Wallny et al., Eur. J. Immunol. 22:655–659, 1992.
Elliott et al., Nature, 348:195–197, 1990.
Michalek et al., Nature, 363:552–554, 1993.
Sebzda et al., Science, 263:1615–1617, 1994.
Hogquist et al., Cell, 76:17–27, 1994.
Gaczynska et al., Nature 365:264–267,1993.
von Boehmer, Nature, 362:696, 1993.
R. Suto et al, Science, 269, 1585–1588, 1995.

Primary Examiner—David Saunders
Attorney, Agent, or Firm—Bereskin & Parr

[57] ABSTRACT

A method of identifying antigens which are capable of being endogenously processed by a cellular secretory pathway comprising: introducing an antigen into a donor cell lacking in MHC class I molecules, incubating in an in vitro medium the donor cells, primed cytotoxic T lymphocytes having specificity for the antigen, and target cells which express MHC class I molecules and are labelled with a detectable intracellular marker, under suitable conditions such that the donor cells remain intact, and measuring the amount of detectable marker released into the incubation medium. A method of assaying a medium for the presence of a substance that affects processing of an endogenously processed antigen in a cellular secretory pathway, and; a method of characterizing a tumor or viral antigen capable of being endogenously processed by a cellular secretory pathway.

21 Claims, 13 Drawing Sheets

METHOD OF IDENTIFYING MHC-CLASS I RESTRICTED ANTIGENS ENDOGENOUSLY PROCESSED BY CELLULAR SECRETORY PATHWAY

FIELD OF THE INVENTION

The invention relates generally to a method of identifying antigens which are capable of being endogenously processed by a cellular secretory pathway and to a method of assaying a medium for the presence of a substance that affects processing of an endogenously processed antigen in the cellular secretory pathway. Further, the invention relates to a method of characterizing cytotoxic T cell antigens capable of being endogenously processed by the cellular secretory pathway.

BACKGROUND OF THE INVENTION

The cytotoxic T lymphocyte (CTL) response is a major component of the immune system, active in immune surveillance and destruction of infected or malignant cells and invading organisms expressing foreign antigens on their surface. The ligand of the antigen-specific T lymphocyte receptor is a complex made up of a peptide fragment of a foreign antigen 8 to 10 amino acids in length, presented in the groove of MHC class I molecules. Unlike B cells, T cells do not recognize intact native antigen molecules. In general, cytotoxic T cell activation requires that the antigen be processed endogenously and cleaved into specific peptide fragments which are presented on the surface of antigen processing cells in association with class I MHC molecules.

MHC class I molecules are normally expressed at the cell surface as ternary complexes formed by a heavy chain of 46 kD, a light chain called $\beta_2$-microglobulin ($\beta_2$m) of 12 kD and a peptide composed of 8–10 amino-acids (van Bleek, G. M. and S. G. Nathenson, *Nature* 348:213, 1990; Zhang, W. et al., *Proc. Natl. Acad. Sci.* USA 89:8403, 1992; Matsumura, M. et al., *Science* 257:927, 1992; and Latron, F., et al., *Science* 257:964, 1992). Formation of the ternary complex is thought to involve transport into the lumen of the endoplasmic reticulum (ER) of peptides generated by protein degradation in the cytoplasm (Nuchtern, J. G. et al., *Nature* 339:223, 1989; Yewdell, J. W. and J. R. Bennink, *Science* 244:1072, 1989; and Cox, J. H. et al., *Science* 247:715, 1990). The study of mutant cell lines selected for their low expression of MHC class I molecules at the cell surface has provided insights into the molecular events required for antigen processing. These studies have allowed the identification of two genes located in the MHC region which encode proteins of the ATP binding cassette (ABC) family. These genes, called TAP-1 and TAP-2, have been implicated in transport of peptides from the cytoplasm to the lumen of the ER (Deverson, E. V. et al., *Nature* 348:738, 1990; Trowsdale, J. et al., *Nature* 348:741, 1990; Spies, T. et al., *Nature* 348:744, 1990; Monaco, J. J. et al., *Science* 250:1723, 1990; Spies, T. and R. DeMars, *Nature* 351:323, 1991; Bahram, S. et al., *Proc. Natl. Acad. Sci.* USA 88:10094,1991; Spies,T. et al., *Nature* 355:644, 1992; Kelly, A. et al., *Nature* 355:641, 1992; Powis, S. H. et al., *Proc. Natl. Acad. Sci.* USA 89:1463, 1992; and Colonna, M. et al., *Proc. Natl. Acad. Sci.* USA 89:3932, 1992). Two other MHC linked genes, LMP-2 and -7 (Monaco, J. J. and McDevitt, 1982, *Proc. Natl. Acad. Sci.* USA 79:3001), are components of the proteasome, a cytoplasmic multicatalytic protease complex, which is likely responsible for some aspects of protein degradation for antigen processing (Ortiz-Navarette, V. et al., *Nature* 353:662, 1991; Brown, M. G. et al., *Nature* 353:355, 1991; Glynne, R. et al., *Nature* 353:357, 1991; Martinez, C. K. and J. J. Monaco, *Nature* 353:664, 1991; Kelly, A. et al., *Nature* 353:667, 1991; Yang, Y. et al., *Proc. Natl. Acad. Sci.* USA 89:4928,1992;Goldberg, A. L. and K. L. Rock, *Nature* 357:375, 1992).

CTL recognize MHC class I molecules bearing endogenously processed foreign or aberrant self proteins, thereby enabling the immune system to respond to intracellular pathogens or tumor transformation. The endogenous cellular processing pathways of MHC class I antigen presentation is thought to require that the antigen be expressed endogenously in the cytoplasm or ER of the presenting cell. The endogenous peptides associate with nascent membrane bound MHC class I molecules before they leave the ER and are eventually presented at the cell surface bound to the MHC class I molecules (Yewdell, W. and J. R. Bennink, 1989, *Science* 244:1072).

Peptides unable to bind MHC Class I because they are in excess or lack the correct MHC binding motif for the MHC haplotype are thus far undetectable by the techniques commonly used in the field and are presumed to be short lived and degraded (Falk et al., *Nature*, 348:248–251, 1990; R ötzschke et al., *Nature*, 348:252–254, 1990). But recent results (Arnold et al., *J. Exp. Med.*, 182:885–889, 1995) suggest that peptides not able to bind to a MHC class I molecule intracellularly may be found bound to heat shock proteins (HSPs) such as gp96. These authors show that cellular antigens are represented by peptides associated with gp96 molecules independently of the MHC class I expressed confirming earlier results by Udono and Srivastava. (*J. Exp. Med.*, 178:1391–1396, 1993; *J. Immunol.*, 152:5398–5403, 1994). Gp96 extracted from a specific cell are able to induce "cross-priming".

Huang et al. (*Science*, 264:96–965, 1994) have elucidated mechanisms in which proteins or peptides may either be exchanged from donor to recipient after release from the cell surface or released following uptake of antigen by the antigen processing donor. Though these phenomena may operate under specific circumstances, they relate to the processing of exogenous antigens rather than endogenous antigens.

Autoimmune disease results from the misdirection of the immune response to self antigens resulting in host tissue damage. Autoimmune diseases may be triggered by infectious agents, such as bacteria and viruses, environmental conditions and certain drugs and toxins. Several mechanisms have been put forward which may account for some, but not all of the features of autoimmunity. For example, autoimmunity may result from the break down of thymic self tolerance mechanisms the mimicry of self proteins by pathogen proteins and from the degeneration of peripheral T cell tolerance.

Although the exact mechanisms are poorly understood, the generation of autoimmune lesions is thought to require an MHC susceptibility allele capable of binding and presenting the antigens that initiate the autoimmune process; reactive T cells specific for those antigens and; target antigens available for presentation by an MHC susceptibility allele to antigen specific T lymphocytes (Sinha, A. A. et al. 1990, *Science* 248:1380). Immune responses initially directed against microbial pathogens are implicated in some autoimmune diseases and autoantibodies specific for a self antigen often also have specificity for viral or bacterial determinants. The mechanisms behind this pathogen-associated autoimmune injury are poorly understood and the sites of autoimmune damage resulting from pathogenic infection are often observed at sites distant from the site of infection. The identification of the target antigens of the autoimmune response may permit the rational development of therapies to block the interaction of these antigens with the autoimmune response, for example by the specific deletion of the anti-self T lymphocytes involved. Accordingly, there is a need for an assay which can be used to identify the target antigens which are recognised by CTL in the generation of an autoimmune response.

CTL also play an important defensive role in the mammalian immune response to destroy invading pathogens, such as bacteria, viruses and microorganisms and defective cells, such as cancer cells. There is a need for an assay which can be used to identify those epitopes of foreign pathogens, precancerous cells and cancer cells which are recognised by CTL. Synthetic peptides have been used in attempts to identify viral and tumor target epitopes recognised by CTL. However, misleading results have been obtained as, frequently CTL may recognize only very short segments of the synthetic peptide. The acid elution method has been used in attempts to identify the short epitopes presented on the cell surface in association with MHC. The epitopes, once identified, may form the basis for the design of therapeutics for T lymphocyte mediated autoimmune disease, pathogenic infections and tumors. In particular, it is expected that the epitopes will be useful for as the basis for vaccines to specifically prime CTL.

SUMMARY OF THE INVENTION

The present inventors have surprisingly found that antigens may be endogenously processed and secreted by the secretory pathway of a cell. The secreted antigens were shown to associate with cell surface MHC class I molecules of bystander target cells.

The present inventors found that virally infected cells or cells transfected with a viral antigen were able to transfer endogenously processed peptides in vitro to recipient target cells for presentation to, and efficient recognition by, primed cytotoxic T lymphocytes (CTL) specific for the virus. Importantly, the present inventors demonstrated that the peptide transfer did not involve viral killing or CTL liberation of peptides from infected cells or the release of membrane-bound MHC class I associated antigen from the cell surface.

Peptide transfer by the virally infected cells was found to be dependent on the presence of TAP transporters. Surprisingly, peptide transfer was found to be independent of the presence of MHC class I molecules, showing that the transferred peptide is not being transported to the cell surface in association with membrane bound MHC class I molecules. Peptide transfer was shown to occur through active transport via the secretory pathway of the cell and an inhibitor of the secretory pathway was shown to inhibit peptide transfer to target cells.

The invention therefore contemplates a method of identifying antigens which are capable of being endogenously processed by a cellular secretory pathway and transferred to bystander target cells for presentation to cytotoxic T lymphocytes, comprising: introducing an antigen into a donor cell lacking in MHC class I molecules; incubating in an in vitro medium the donor cells, primed cytotoxic T lymphocytes having specificity for the antigen, and target cells which express MHC class I molecules and are labelled with a detectable intracellular marker, under suitable conditions such that the donor cells remain intact, and; measuring the amount of detectable marker released into the incubation medium.

Preferably the antigen is a viral, bacterial or tumor antigen. In an embodiment the antigen is VSV, an allo peptide or a self peptide.

The invention also relates to a method of assaying a medium for the presence of a substance that affects processing of an endogenously processed antigen in a cellular secretory pathway, comprising: incubating in an in vitro medium a donor mammalian cell having an antigen capable of being endogenously processed by a secretory pathway of the donor cell, a target cell expressing MHC class I molecules and labelled with a detectable intracellular marker, and primed cytotoxic lymphocytes having specificity for the antigen, in the presence or absence of a substance that is suspected of affecting processing of endogenously processed antigen in the cellular secretory pathway, under suitable conditions such that the donor cells remain intact, and; measuring the amount of detectable marker released into the medium in the presence or absence of the substance.

In an embodiment, the donor cell lacks MHC class I molecules. Any cell expressing MHC Class I molecules may be used as the target cell. In a preferred embodiment, mammalian target cells, including human cells, may be used. In a particular embodiment the antigen is VSV and the target cell is RMA.

It is expected that substances that affect processing of an endogenously processed antigen in a cellular secretory pathway will be useful as immunomodulators for stimulating or inhibiting the immune response.

The invention still further relates to a method of characterizing a tumor or viral antigen comprising: obtaining, from a mammal, tumor cells or virally infected cells and primed cytotoxic T lymphocytes having specificity for the tumor or virally infected cells; preparing a cDNA library from the tumor or virally infected cells and expressing the cDNA library in transfected host cells; incubating in a medium, transfected host cells, target cells expressing MHC class I molecules and labelled with a detectable intracellular marker and the primed cytotoxic lymphocytes under suitable conditions such that the donor cells remain intact, and; measuring the amount of the detectable marker released into the medium and identifying those transfected cells capable of causing lysis of the target cells and characterizing the transfected DNA and expression product of the transfected DNA of the identified transfected cells. As will be appreciated, the method may also be employed to characterize alloantigens, self antigens and antigens of other pathogens, such as bacteria, protozoa, or other microorganisms or parasites. Transiently transfected COS cells may be employed in the methods of the invention.

The present invention also contemplates the cloning of genes encoding the antigens characterized by the methods of the invention and vaccines incorporating the characterized antigens and epitopes.

These and other aspects of the present invention will become evident upon reference to the following detailed description and attached drawings. In addition, reference is made herein to various publications, which are hereby incorporated by reference in their entirety.

DESCRIPTION OF THE DRAWINGS

The invention will be better understood with reference to the drawings in which.

DETAILED DESCRIPTION OF THE INVENTION

Figure 1A:
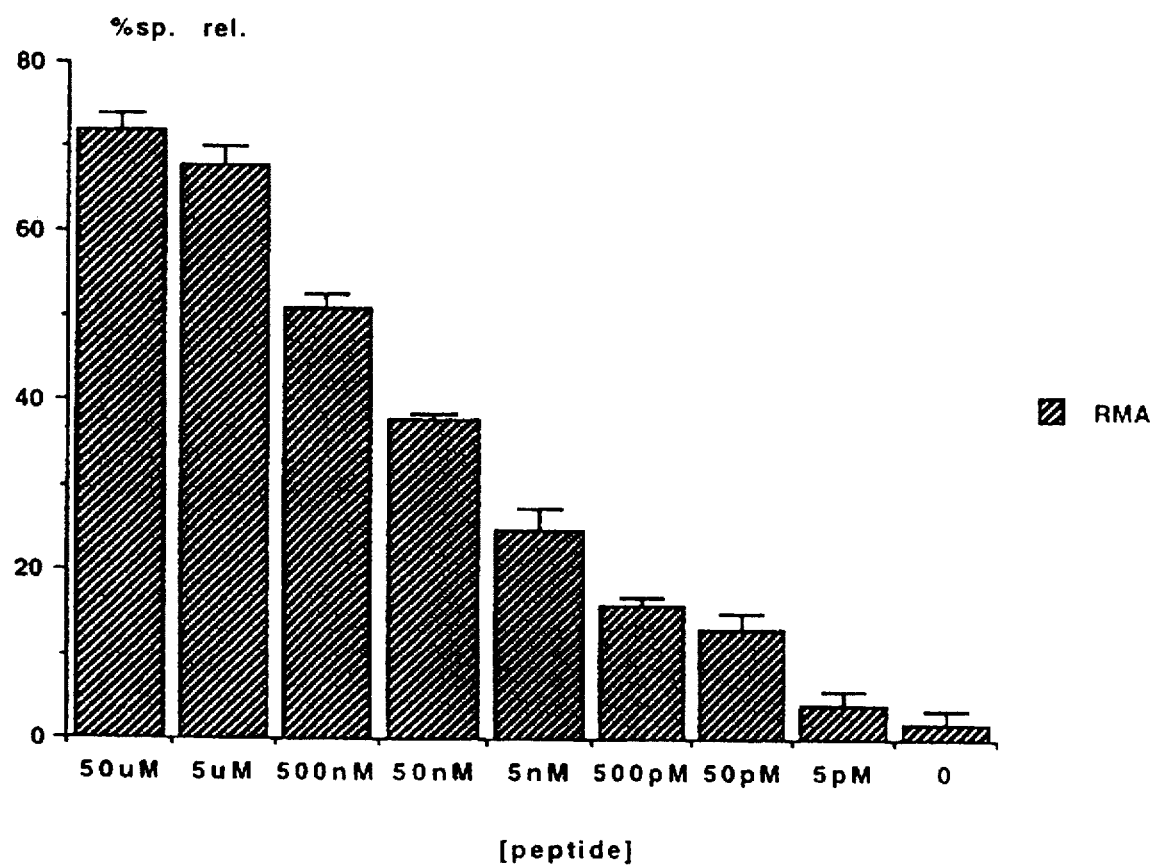
FIG. 1A is a bar graph showing the concentration of VSV-N peptide which yields a particular percentage of cytotoxicity.

As hereinbefore mentioned, the present inventors have demonstrated that antigens may be endogenously processed and secreted by the secretory pathway of a cell and cells are able to transfer endogenously processed peptides in vitro to recipient target cells for presentation to, and efficient recognition by, specifically primed CTL.

The present inventors demonstrated that the peptide transfer is not dependent on viral killing or CTL liberation of peptides from infected cells or the release of membrane-bound MHC class I associated antigen from the cell surface.

Peptide transfer by the virally infected cells was found to be dependent on the presence of TAP transporters. Surprisingly, peptide transfer was found to be independent of the presence of MHC class I molecules, showing that the transferred peptide is not being transported to the cell surface in association with membrane bound MHC class I molecules. Peptide transfer was shown to be occurring through active transport via the secretory pathway of the cell and an inhibitor of the secretory pathway was shown to inhibit peptide transfer to target cells.

Accordingly as hereinbefore mentioned, the present invention provides a method of identifying antigens which are capable of being endogenously processed by a novel cellular secretory pathway and transferred to bystander target cells for presentation to cytotoxic T lymphocytes, comprising: introducing an antigen into a donor cell lacking in MHC class I molecules;, incubating in an in vitro medium the donor cells, primed cytotoxic T lymphocytes having specificity for the antigen, and target cells which express MHC class I molecules and are labelled with a detectable intracellular marker, under suitable conditions such that the donor cells remain intact, and; measuring the amount of detectable marker released into the incubation medium.

Antigens which require endogenous processing for presentation to CTL are well known. The majority of cytotoxic T lymphocytes recognize epitopes of MHC class I restricted antigens in association with class I major histocompatibility molecules. Such antigens are usually referred to as MHC class I restricted antigens. MHC class I restricted antigens are those antigens which require endogenous cell processing and whose epitopes are presented on the cell surface by MHC class I molecules for recognition by CTL.

Antigens suitable for endogenous processing may be derived from any protein endogenous to a cell, for example from normal, viral, bacterial, defective or tumor proteins. The peptides resulting from endogenous processing of the antigen have the appropriate amino acid sequence for interaction with, and presentation by, MHC class I molecules. The resulting peptides expressed at the cell surface may be detected by CTL and can be extracted from cells, for example by treating whole cells with trifluoroacetic acid. Examples of MHC class I antigens include viral antigens, such as influenza nucleoprotein, vesicular stomatitis virus N protein (VSV), tumor antigens, HSV, protozoal, bacterial or parasitic antigens, allopeptides, self peptides, HIV peptides and endogenous peptides and other viral peptides. Examples of MHC class I antigens are provided in Rammensee, et al., 1995 (*Immunogenetics*, 41:178–228).

A cellular secretory pathway for endogenously processing antigens has not heretofore been described. By cellular secretory pathway is meant a route of intracellular antigen processing, whereby endogenous antigen is degraded in the cell and processed into a peptide which is secreted from the cell in a form suitable for interaction with cell surface MHC class I molecules of a bystander target cell and the translocation system. The cellular secretory pathway may be distinguished from the known routes of endogenous antigen processing, which are dependent on the presence of MHC class I molecules in the cell, as the cellular secretory pathway is not dependent on the presence of MHC class I molecules in the antigen processing cell.

The cellular secretory pathway may be further characterized as being dependent on the expression of functional TAP transporters in the cell and it is specifically inhibited by inhibitors of protein secretion, such as Brefeldin A. It will be appreciated that compounds which disrupt the Golgi or interfere with exocytosis of secretory proteins will inhibit protein secretion from the cell. In particular, the cellular secretory pathway is inhibited by Brefeldin A, preferably at concentrations which inhibit protein secretion but do not harm cell viability, for example from 1 to 10 μg/ml, more preferably from 3 to 6 μg/ml, most preferably about 4 to 5 μg/ml.

It should be noted that the sensitivity of the cellular secretory pathway to specific inhibitors of protein secretion such as Brefeldin A, clearly distinguishes the cellular secretory pathway from the pathway for processing exogenous antigens, whereby exogenous antigens may become associated with MHC molecules at the cell surface. The processing of exogenous antigens is not affected by Brefeldin A.

Suitable donor cells for use in the method of the invention, for identifying antigens which are capable of being endogenously processed by a cellular secretory pathway and transferred to bystander target cells for presentation to CTL, are any animal cells, preferably mammalian cells which are lacking in cell surface expression of MHC class I molecules. As noted above, the donor cells lacking in cell surface expression of MHC class I molecules are used in the method of the invention in order to distinguish the novel cellular secretory pathway from the known pathway of endogenous antigen processing, which depends on the presence of MHC class I molecules, whereby peptide processed from the endogenous antigen is transported to the cell surface only in association with MHC class I molecules. However, with suitable controls, it is also anticipated that cells having MHC Class I molecules could be used as donor cells.

Mammalian cells lacking in cell surface expression of MHC class I molecules may be selected by methods known in the art. Suitable cells may lack or have a non-functional defect in the appropriate genes encoding MHC class I molecules, have a mutation in the MHC locus, be unable to transport MHC class I molecules to the cell surface or, be deficient in the expression of class I molecules. It is also anticipated that non-mammalian cells may be used as donor cells, such as avian, amphibian, reptile, fish and insect cells.

Donor cells lacking in cell surface expression of MHC class I molecules may be selected for example by infecting a cell with a recombinant viral vector such as VSV, and testing for lysis by VSV specific CTL. FACS analysis may also be used to detect MHC class I molecules on the surfaces of a putative donor cell. The biosynthesis and intracellular transport of MHC class I molecules may also be biochemically characterized. For example, endo H which cleaves N-linked oligosaccharides only when they are in the high mannose form characteristic of proteins present in the ER and cis-Golgi complex may be used to measure intracellular transport. Pulse-chase methodology may also be utilized to confirm donor cells lacking in cell surface expression of MHC class I molecules. The above methods are illustrated in part in Restifo, N. P. et al. (1993, *J. Exp. Med.* 177:265).

Examples of cells which express low levels of MHC class I molecules are tumor cells derived from colon, breast, lung mesothelioma and lung cancers of the small cell histology (See Restifo, N. P., supra 1993).

Examples of suitable donor cells include cells lacking in β2-microglobulin, which is required for the intracellular transport of MHC class I molecules to the cell surface. Examples of cells deficient in β2 microglobulin include murine R1E cells and the human Daudi cell line. Tumor cells deficient in cell surface MHC class I molecules may also be used. Suitable donor cells include human Ti (Salter, R. O. and P. Cresswell, 1986, EMBO J. 5:943), murine Ltk-(H-2$^K$), NIH 3T3 (H-2$^d$), R1.E (Williams et al. 1989, *J. Immunol.* 142:1796). LCL cells with chromosome deletion, T2 cells and mouse cell lines expressing HLA for allotransfer may be used in the methods of the invention.

Preferably, donor cells should be selected which are not defective in other aspects of endogenous antigen processing, for example the proteasome components and the TAP transporters. Cells deficient in certain proteasome or TAP transporter components in addition to MHC class I components may be adapted for use as donor cells by correcting the proteasome or transporter deficiency. For example if the cell is deficient in TAP 1 or TAP 2, such as tumor cells, this defect may be corrected by introducing a nucleotide sequence encoding TAP 1 and/or TAP 2 into the cell.

It is also contemplated that the method of the invention for identifying antigens capable of being processed by a cellular secretory pathway and transferred to bystander target cells may be carried out using donor cells which are not necessarily deficient in surface expression of MHC class I as long as suitable controls are performed. Suitable controls are those which serve to distinguish the novel cellular secretory pathway from the known MHC class I dependent pathway of endogenous antigen processing. Such controls should be performed to rule out the possibility that MHC class I bound antigens at the surface of the donor cell are released into the medium to associate with the target bystander cells. For example, the cells may be pulsed with synthetic peptide and followed for release or antisense nucleotide molecules may be used to inhibit MHC expression. Use of supernatant from VSV infected cells can sensitize cells for VSV specific killing.

The antigen to be identified in the method of the invention may be naturally occurring in the donor cell or may be introduced into the donor cell by methods known in the art. The antigen may be introduced into the cell by microinjection. The antigen may also be introduced into the donor cell by introducing a nucleic acid molecule encoding the antigen into the donor cell under suitable conditions to obtain expression of the antigen in the donor cell.

The nucleic acid molecule encoding an antigen may be introduced into the donor cell under the control of a suitable promoter. The nucleic acid encoding the antigen may be readily synthesized using techniques known in the art. A nucleic acid molecule encoding an antigen may be isolated and sequenced, for example, by synthesizing cDNAs from RNA and using rapid amplification of cDNA ends (RACE, Frohman, et al., 1988) using oligonucleotides specific for the antigen, and analyzing the sequences of the clones obtained following amplification. Oligonucleotides specific for the antigen may be identified by comparing the nucleic acid sequence to known sequences of the antigen. Nucleic acid molecules encoding the antigen may also be constructed by chemical synthesis and enzymatic ligation reactions using procedures known in the art. The sequence encoding the antigen may also be prepared using recombinant DNA methods.

Nucleic acid molecules having a sequence which codes for the antigen may be incorporated in a known manner into an appropriate expression vector which ensures good expression of the antigen or part thereof. Possible expression vectors include but are not limited to cosmids, plasmids, or modified viruses, so long as the vector is compatible with the donor cell used.

It is contemplated that the nucleic acid molecules described herein contain the necessary elements for the transcription and translation of the inserted protein antigen-sequence. Suitable transcription and translation elements may be derived from a variety of sources, including bacterial, fungal, viral, mammalian, or insect genes. Selection of appropriate transcription and translation elements is dependent on the donor cell chosen as discussed below, and may be readily accomplished by one of ordinary skill in the art. Examples of such elements include: a transcriptional promoter and enhancer or RNA polymerase binding sequence, a ribosomal binding sequence, including a translation initiation signal. Additionally, depending on the donor cell chosen and the vector employed, other genetic elements, such as an origin of replication, additional DNA restriction sites, enhancers, and sequences conferring inducibility of transcription may be incorporated into the expression vector. It will also be appreciated that the necessary transcriptional and translation elements may be supplied by the nucleic acid molecule encoding native antigen.

The nucleic acid molecules may also contain a reporter gene which facilitates the selection of transformed or transfected donor cells. Examples of reporter genes are genes encoding a protein such as β-galactosidase, chloramphenicol acetyltransferase, firefly luciferase, or an immunoglobulin or portion thereof such as the Fc portion of an immunoglobulin preferably IgG. In a preferred embodiment, the reporter gene is lac Z. Transcription of the reporter gene is monitored by changes in the concentration of the reporter protein such as β-galactosidase, chloramphenicol acetyltransferase, or firefly luciferase. This makes it possible to visualize and assay for expression of the antigen in the donor cell.

Nucleic acid molecules comprising a sequence encoding an antigen can be introduced into donor cells via transformation, transfection, infection, electroporation etc. Methods for transforming transfecting, etc. host cells to express foreign DNA are well known in the art (see, e.g., Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989, all of which are incorporated herein by reference).

Suitable expression vectors for directing expression in mammalian donor cells generally include a promoter, as well as other transcriptional and translational control sequences. Common promoters include SV40, MMTV, metallothionein-1, adenovirus EIa, CMV, immediate early, immunoglobulin heavy chain promoter and enhancer, and RSV-LTR. Protocols for the transfection of mammalian cells are well known to those of ordinary skill in the art. Representative methods include calcium phosphate mediated electroporation, retroviral, and protoplast fusion-mediated transfection (see Sambrook et al., supra).

In an embodiment, the nucleic acid molecule may be introduced into the donor cell in a viral vector, preferably a vaccinia viral vector, most preferably attenuated. Suitable promoters for use with vaccinia viruses include P7.5 Cochran, M. A. et al, 1985, *J. Virol.* 54:30), P11 (Bertholet, C. et al, 1985, *Proc. Natl. Acad. Sci.* USA, 82:2096), CAE-1 (Patel, D. D. et al, 1988, *Proc. Natl. Acad. Sci.* USA 85:9431).

The nucleic acid molecule may be inserted into a non-essential site of a vaccinia viral vector. Such non-essential sites are well known and are described, for example, in Perkus et al, 1986, *Virology* 152:285; Hruby et al, 1983, *Proc. Natl. Acad. Sci.* USA 80: 3411 and; Weir and Moss, 1983, *J. Virol.* 46:530). Recombinant viruses expressing the antigen may be readily identified using techniques known in the art and discussed, for example, in Moss, B, 1992, (*Curr. Topics Microbiol. Immunol.* 158:25).

It will be appreciated that the antigen may also be an endogenous antigen which naturally occurs in the donor cell, for example an endogenous tumor antigen. Antigens of intracellular pathogenic agents may be introduced into the donor cell by infecting the donor cell with the pathogenic agent. Examples of intracellular pathogenic agents include viruses, such as HIV, influenza virus, herpes virus, papilloma virus, retroviruses, and rickettsia, and intracellular bacterial pathogens, and protozoan parasites, such as malaria, trypanosomes and Leishmania.

Primed CTL having specificity for the antigen may be obtained by known methods. Specific primed cytotoxic T lymphocytes may be obtained from the spleen, blood or lymph of a mammal infected with an intracellular pathogen or having a tumor expressing the antigen of interest.

Primed CTL having specificity for the antigen may also be obtained by immunizing a mammal with the antigen. Methods for immunization of mammals to prime cytotoxic immunity are described for example in Rock, K. L. et al. (1993, *J. Immunol.* 150:1244) and Moss, B. (1990, *Seminars in Immunol.* 2:317). Suitable immunization protocols include administering the antigen or peptide fractions thereof together with β2-microglobulin, or administering a recombinant viral vector encoding the antigen or peptide fractions of the antigen.

Suitable target cells for use in the method of the invention include mammalian cells which express MHC class I molecules on their surface. The target cells and primed CTL may be selected from the same mammal. It will be appreciated that target cells should be selected which do not themselves express the antigen of interest. For example where the antigen of interest is a tumor antigen or an intracellular pathogenic agent of a mammal, a suitable target cell may be selected from non-tumor cells or uninfected cells of the mammal. It will be appreciated that cells, other than those from the mammal may also be used, for example, cells from another animal may be transfected with the appropriate MHC.

Suitable incubation media and conditions for maintaining mammalian cells intact during in vitro culture are well known. The target cells are labelled with a detectable intracellular marker. The intracellular marker should be one which is not readily released from the target cell in the absence of cell damage and lysis of the target cell. Suitable intracellular markers include [$^{51}$]Cr, fluorescent markers or Beckman reagent.

An antigen which is endogenously processed by a cellular secretory pathway and transferred to bystander target cells for presentation to cytotoxic T lymphocytes may be identified based on the release of detectable intracellular label into the medium, or based on some other measure of the death of target cells, for example based on the detection of thymidase or DNA fragments.

As hereinbefore noted, the present invention also provides a method of assaying a medium for the presence of a substance that affects processing of an endogenously processed antigen in a cellular secretory pathway, comprising: incubating in an in vitro medium a donor mammalian cell having an antigen capable of being endogenously processed by a secretory pathway of the donor cell, a target cell expressing MHC class I molecules and labelled with a detectable intracellular marker, and primed cytotoxic lymphocytes having specificity for the antigen, in the presence or absence of a substance that is suspected of affecting processing of endogenously processed antigen in the cellular secretory pathway, under suitable conditions such that the donor cells remain intact, and; measuring the amount of detectable marker released into the medium in the presence or absence of the substance.

It will be appreciated that substances which stimulate or inhibit the processing of an endogenously processed antigen in a cellular secretory pathway will, in the method of the invention, result in increased or decreased amounts respectively of detectable marker being released into the medium over a certain time period compared to control incubations carried out in the absence of the substance.

The method may be used to specifically assay for substances that affect processing, rather than secretion, of the endogenously processed antigen in the cellular secretory pathway by simultaneously determining the effect of the substance on secretion of a protein that is known to be secreted from the donor cell, such as growth hormone for example.

The method of the invention may therefore be used to identify substances which inhibit or stimulate processing of antigen from a cell by the cellular secretory pathway. It is anticipated that substances which inhibit or stimulate antigen secretion by the cellular secretory pathway will have an immunomodulating effect when administered to a mammal in vivo and be useful as pharmaceuticals for treating tumors and infection with intracellular pathogens such as viruses.

Substances which inhibit antigen processing may also be useful for the treatment of autoimmune diseases, particularly diseases of MHC class I associated autoimmune disorders such as the HLA-B27 related spondyloarthropathies, including ankylosing spondylitis, Reiter's syndrome and reactive arthropathy, Sjogren's syndrome, rheumatoid arthritis, type I polyendocrine failure, multiple sclerosis, hypothyroidism, Hashimoto's disease, Graves disease and psoriasis vulgaris, and autoimmune diseases resulting from an excessive immune response to foreign antigens of intracellular pathogens. Substances which inhibit antigen secretion may also be useful for the treatment of viral infections where the antigenic load is high, in order to prevent exhaustion and depletion of CTL, leading to the development of immunological tolerance. Substances which inhibit antigen secretion may also be used to treat organs prior to transplant to avoid rejection and to treat mammals with transplanted tissue or organs to decrease the immune rejection response.

Substances which stimulate antigen secretion may be useful for the treatment of tumors and for intracellular pathogens, where the tumor or pathogenic antigens are generally sequestered from the immune system and not appropriately presented on the cell surface by MHC class I molecules.

As hereinbefore mentioned, the invention still further provides a method of characterizing a tumor or viral antigen capable of being endogenously processed by a cellular secretory pathway comprising: obtaining, from a mammal, tumor or virally infected cells and primed cytotoxic T lymphocytes having specificity for the tumor or virally infected cells; preparing a cDNA library from the tumor or virally infected cells and expressing the cDNA library in transfected host cells; incubating in a medium, transfected host cells, target cells expressing MHC class I molecules and labelled with a detectable intracellular marker and the primed cytotoxic lymphocytes under suitable conditions such that the donor cells remain intact, and; measuring the amount of the detectable marker released into the medium and identifying those transfected cells capable of causing lysis of the target cells and characterizing the transfected DNA of the identified transfected cells.

The mammal from which the tumor cells and primed CTL are obtained may be a mammal having a naturally occurring tumor or a tumor induced by means of a tumorigenic substance, or may be a mammal into which a tumor has been introduced. The mammal may be a human having a tumor and may also be a non-human mammal into which a human tumor or human tumor cell line has been introduced. Human tumor cell lines are well known, see for example Restifo, N. B. et al. (1993) *J. Exp. Med.* 177:265. cDNA expression libraries may be constructed, following known techniques, using mRNA from tumor cells.

cDNA clones coding for antigens processed by the cellular secretory pathway may be identified, subcloned and sequenced. The cDNA sequences, or fragments thereof may be used as hybridization probes to isolate genomic DNA encoding for the antigen. The invention therefore provides a method for cloning the gene encoding the tumor antigen and for isolating the antigen. Identification and isolation of the antigen will permit studies of the role of the antigen in the development of the cytotoxic T lymphocyte immune response to the tumor and the development of substances which affect the development of this immunity as stimulators or inhibitors of the immune response. Vaccines may be developed using the genes, for example in retroviral vaccines. The antigens expressed may also be used as the basis for vaccines. It is contemplated that the antigens will bind to the empty MHC 2 molecules which occur on many tumors to aid immune recognition of the tumors.

Nucleic acid molecules encoding tumor antigens may be isolated and sequenced and incorporated into a recombinant molecule which ensures good expression of the antigen or part thereof. In general, a recombinant molecule of the invention contains a nucleic acid molecule, or an oligonucleotide fragment thereof, encoding the antigen and an expression control sequence operatively linked to the nucleic acid molecule or oligonucleotide fragment. A nucleic acid molecule of the invention or an oligonucleotide fragment thereof, may be incorporated into a plasmid vector, for example, pECE. Suitable regulatory elements may be derived from a variety of sources, including bacterial, fungal, viral, mammalian, or insect genes. Selection of appropriate regulatory elements is dependent on the host cell chosen, and may be readily accomplished by one of ordinary skill in the art. Examples of regulatory elements include: a transcriptional promoter and enhancer or RNA polymerase binding sequence, a ribosomal binding sequence, including a translation initiation signal. Additionally, depending on the host cell chosen and the vector employed, other genetic elements, such as an origin of replication, additional DNA restriction sites, enhancers, sequences conferring inducibility of transcription, and selectable markers, may be incorporated into the expression vector.

The antigen or parts thereof, may be obtained by expression in a suitable host cell using techniques known in the art. Suitable host cells include prokaryotic or eukaryotic organisms or cell lines, for example, yeast, *E. coli* and mouse NIH 3T3 cells may be used as host cells. The protein or parts thereof may be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

DNA sequences encoding the antigen, or a part thereof, may be expressed by a wide variety of prokaryotic and eukaryotic host cells, including bacterial, mammalian, yeast or other fungi, viral, plant, or insect cells. Methods for transforming or transfecting such cells to express foreign DNA are well known in the art (see, e.g., Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,935,349; Hagen et al., U.S.

Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989, all of which are incorporated herein by reference).

Preferably, the tumor antigen is expressed in a mammalian cell. Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573) L cells, NIH 3T3 cells and NS-1 cells. Suitable expression vectors for directing expression in mammalian cells generally include a promoter, as well as other transcriptional and translational control sequences. Common promoters include SV40, MMTV, metallothionein-1, adenovirus E1a, CMV, immediate early, immunoglobulin heavy chain promoter and enhancer, and RSV-LTR. Protocols for the transfection of mammalian cells are well known to those of ordinary skill in the art. Representative methods include calcium phosphate mediated transfection, lipofection-mediated transfection, electroporation, retroviral, and protoplast fusion-mediated transfection (see Sambrook et al., supra).

The tumor antigen may be prepared by culturing the host/vector systems described above, in order to express the recombinant antigen.

It will be appreciated that the method of the invention may also be used to characterize antigens, other than tumor antigens, that are capable of being endogenously processed by a cellular secretory pathway. For example, the method will also be useful for characterizing antigens of intracellular pathogens, such as viruses, bacteria and protozoa.

The expression product of the transfected DNA of those transfected host cells capable of causing lysis of the target cells may be directly characterized. Lysis results from CTL recognition of an antigenic peptide presented by the MHC class I molecules on the surface of the target cells. Accordingly, the MHC class I molecules with their associated antigenic peptides may be isolated from the incubation medium and the antigenic peptide extracted using known techniques, as described, for example in Van Bleek, G. M. and S. G. Nathenson, 1990, Nature 348:213; and Rammensee et al., 1995, Immunogenetics, 41:178–228. The antigenic peptides identified may be the dominant T cell epitope of the antigen.

The MHC Class I fractions may be isolated from the incubation medium by immunoprecipitation and a low molecular weight peptide fraction may be extracted by acid denaturation followed by centrifugation. The low molecular weight peptide fraction may be separated by reverse phase HPLC. The prominent peak corresponding to the antigenic peptide recognised by the T cell receptor may be identified by comparison with the profile obtained from control target cells incubated with non-transfected donor cells. The prominent peak corresponding to the antigenic peptide may be further analyzed, for example by microsequencing. Antigenic peptides may also be identified by peptide scan methods or deletion analysis.

The DNA of those transfected cells capable of causing lysis of the target cells may also be characterized. In an embodiment, all of the transfected host cells capable of causing lysis may be pooled, their DNA extracted and retransfected into host cells for one or more further rounds of screening. Ultimately a single transfected DNA sequence, expressing antigen capable of causing lysis, may be identified, sequenced and expressed for further characterization by sequencing.

The method of the invention thus provides a method for identifying the antigenic peptide or epitope from tumor or viral antigens recognised by the T cell receptor.

All publications, patents and patent applications referred to herein are incorporated by reference in their entirety to the same extent as if each individual publication, patent or patent application was specifically and individually indicated to be incorporated by reference in its entirety.

The following examples are offered by way of illustration only, and not by way of limitation.

EXAMPLES

Example 1

Virally infected RMA cells transfer peptides to recipient chromium labelled uninfected RMA cells A system for investigating surrogate antigen processing was developed using the immunodominant epitope of the VSV-N protein (VSV-N 52-59) presented by the $K^b$ molecules of the MHC class I.

CTL effectors specific for VSV were generated by injecting C57BL/6 mice with VSV ($5 \times 10^6$ TCID$_{50}$ per site) in the ears and/or foot pads. Five days later the draining lymph nodes were removed and lymphocytes cultured at $4 \times 10^6$ cells/ml for 3 days in the absence of stimulation.

Cold targets were prepared as follows: RMA cells were treated with VSV (MOI of 2) for 12 to 18 hours, and subsequently washed three times. Hot targets were prepared as follows: RMA cells were treated with [$^{51}$]Cr for two hours and subsequently washed three times.

Cold targets were diluted two-fold starting with $2 \times 10^5$ cells per well. Each well received $1 \times 10^6$ effectors and $1 \times 10^4$ hot targets. Effectors, cold and hot targets were incubated together in V-bottom 96-well plates for 4 hours, followed by removal of 100 µl of supernatant which was then counted for radioactivity released.

FIG. 1A shows the concentration of VSV-N peptide which yields a particular percentage of cytotoxicity. Fifty percent of maximum chromium release was yielded at a peptide concentration of 50 pM. This result was highly reproducible.

In order to determine the RMA dose response, the effector cells were tested against hot RMA target cells pulsed with peptide VSV N52-59 at different concentrations for 2 hours in a dose response.

Figure 1B:
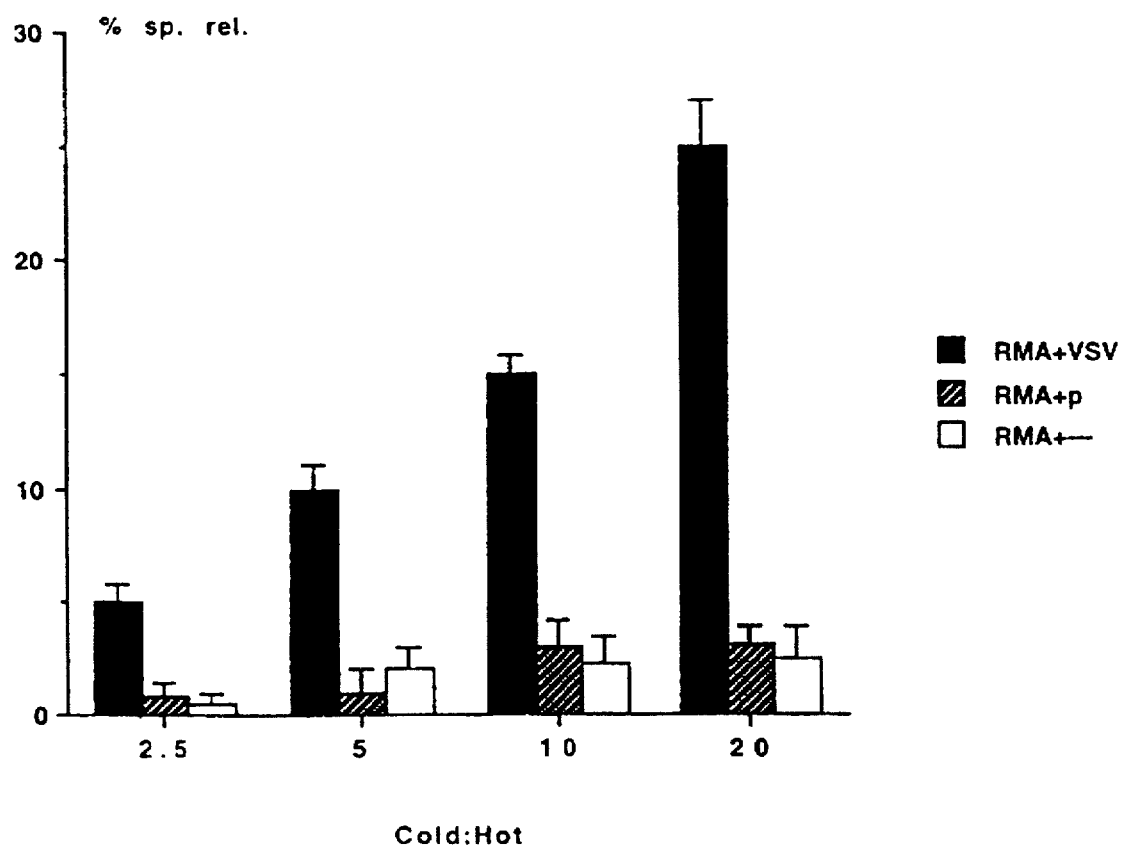
FIG. 1B is a bar graph showing the ability of VSV infected cells (RMA+VSV), cells pulsed with synthetic peptide (RMA+p) and control cells (RMA+−) to generate and transfer peptides to uninfected, chromium laden, target cells.

The effector cell population was tested against hot RMA target cells pulsed with peptide VSV N52-59 at different concentrations for 2 hours in a dose response. The ability of cells to process and transfer the generated peptides to uninfected cells was addressed by infecting cells not labelled with chromium and then incubating these cells together with uninfected target cells which were chromium laden (FIG. 1B). When wild-type RMA infected cells were used as the peptide donors we found that uninfected RMA cells were killed efficiently; greater than 25% at a cold/hot of 20/1. It is suggested from our standard curve that the chromium labelled target cells had been exposed to a minimum of 10-50 pM of peptides derived from the VSV infected cells.

In FIG. 1B, a control in which the surrogate cells were pulsed with a high concentration of synthetic peptide was included to examine if the peptide could be exchanged from the plasma membrane to trigger recognition by T cells on bystander targets. Cells pulsed with saturating concentrations of antigenic peptides were found to not be able to efficiently transfer peptides to recipient cells. Although this may happen over time, as suggested by Huang et al. (A. Y. C. Huang, et al. Science 264:961, 1994), we found no evidence for this in our assays.

RMA cells were infected for 12 hours (RMA+VSV) prior to the CTL assay, or alternatively, RMA cells were treated with VSV immediately prior to adding the effectors (RMA.4+VSV). The effector to target ratios ranged from 12.5:1 to 100:1.

Figure 1C:
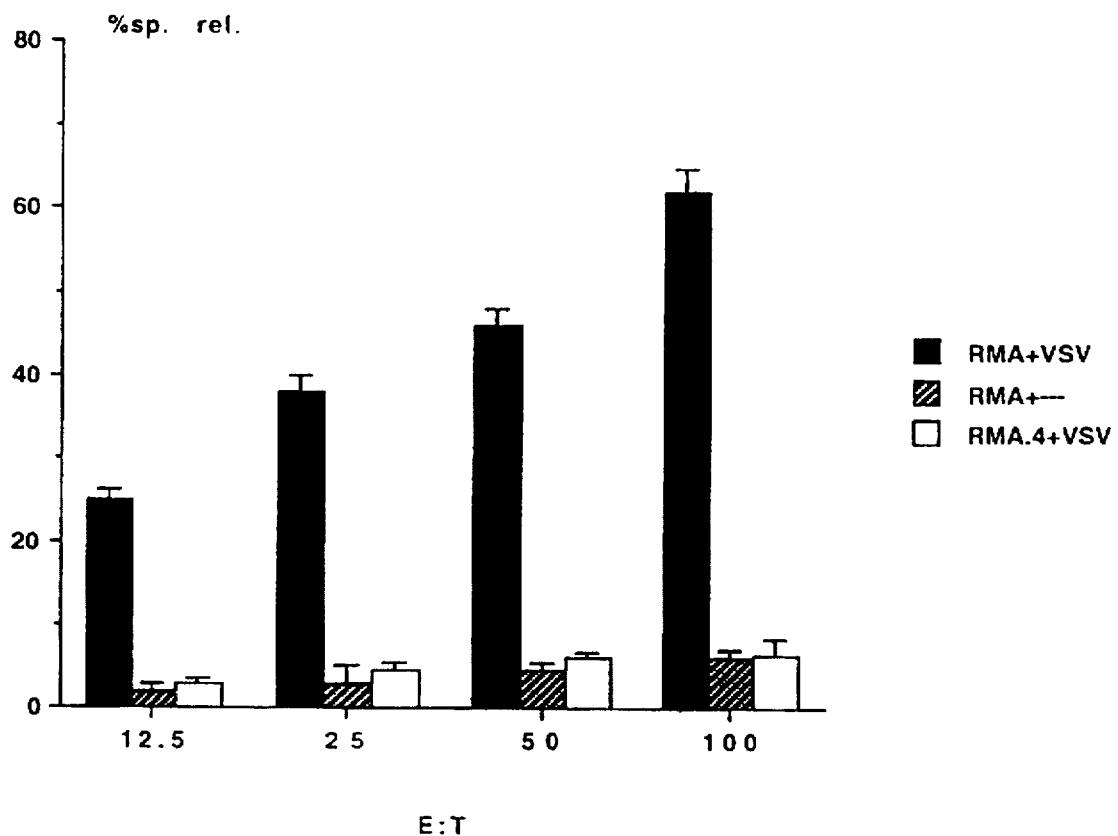
FIG. 1C is a bar graph showing the ability of RMA cells infected for 12 hours (RMA+VSV), or treated with VSV immediately prior to adding the effectors (RMA.4+VSV) to generate and transfer peptides to uninfected, chromium laden, target cells.

The time frame of the assay (4h) did not allow chromium loaded cells to be infected with VSV, process proteins, and subsequently be recognized by specific CTL (FIG. 1C). In addition, our results using cold target competition assays indicate that the peptide transferred was the immunodominant VSV-N 52-59 peptide (data not shown). In summary, virally infected RMA cells were shown to be extremely efficient at transferring peptides to recipient chromium labelled uninfected RMA cells.

Example 2

Ability of human T1(HLA-A,B,C), murine Ltk- (H-2$^k$) and NIH 3T3 (H-2$^d$) cells to transfer peptides to recipient RMA cells In order to examine if the underlying mechanism for transfer involves viral killing or CTL liberation of peptides from infected cells, we studied cells which are not recognized by VSV specific K$^b$ restricted CTL but retain their ability to be infected by virus. We examined the ability of human T1 (R. D. Salter and P. Cresswell. EMBO J. 5:943, 1986), murine Ltk- (H-2$^k$), and NIH 3T3 cells (H-2$^d$) to transfer peptides to recipient uninfected RMA (H-2$^b$) cells.

Figure 2A:
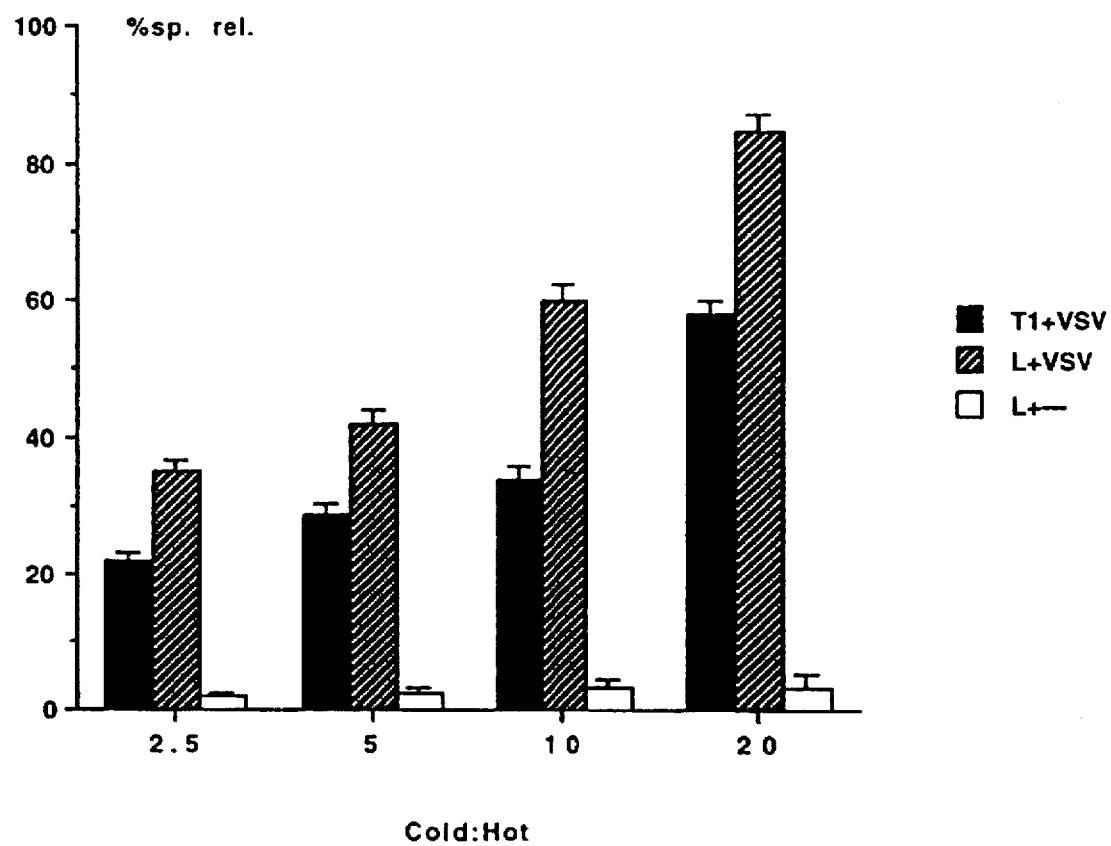
FIG. 2A is a bar graph showing the ability of human T1, or mouse Ltk-(L), and NIH3T3 (NIH) cells treated with or without (L+−−) VSV to generate and transfer peptides to uninfected, chromium laden, target cells.

CTL were generated as described in Example 1 herein. T1, Ltk-(L), NIH3T3 (NIH) and CMT.1–4 cells were treated with or without VSV (MOI of 2) for 12 to 18 hours and subsequently washed 3 times. Hot targets were RMA cells treated with [$^{51}$]Cr for 2 hours and subsequently washed 3 times. The results are shown in FIGS. 2A and 2C.

In order to determine the CTL response T1,L, and NIH+ VSV, Ti, Ltk-(L), and NIH3T3 (NIH) cells were added to effectors after VSV infection and [$^{51}$]Cr labelling to examine whether or not they are recognized as targets for VSV-specific CTL at different effector to target ratios (E:T). Mock infected Ltk- cells (L+—) were used as negative controls.

Figure 2B:
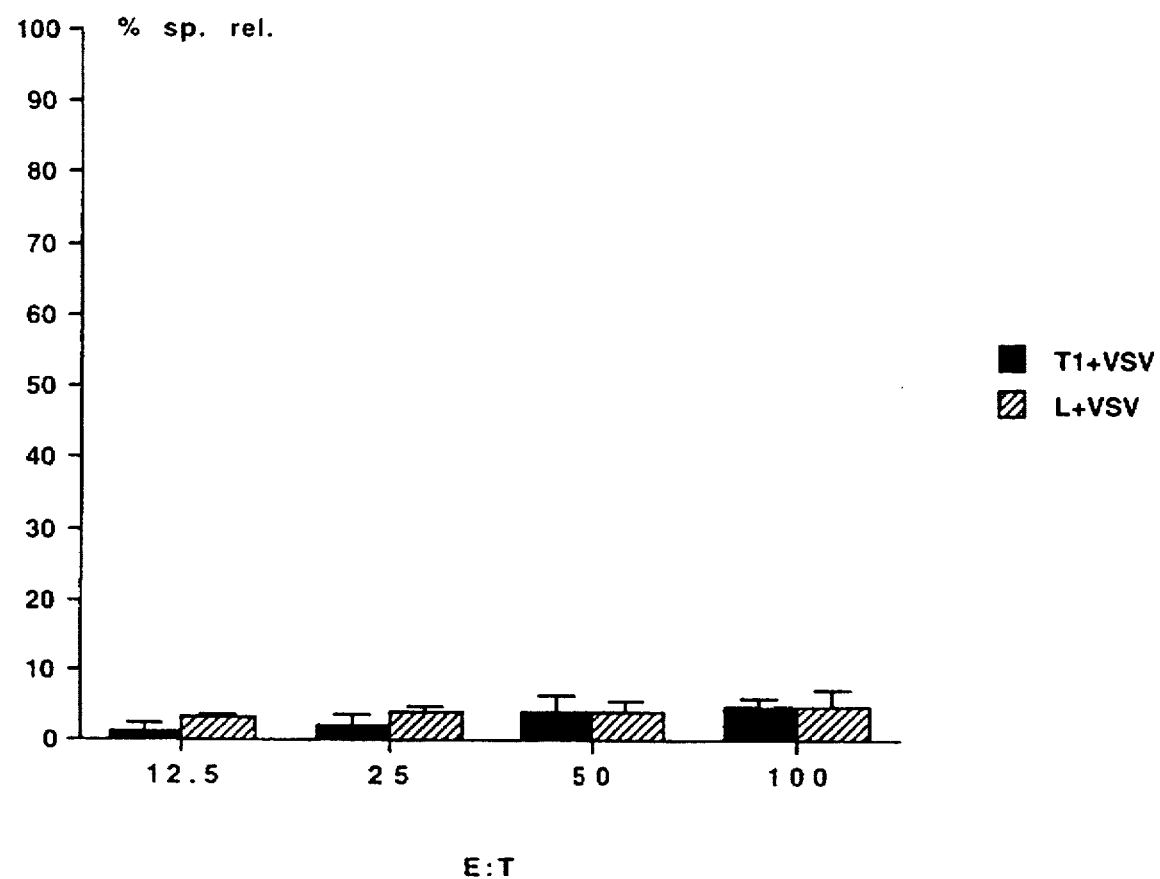
FIG. 2B is a bar graph showing that T1, L, and NIH 3T3, cells were not lysed by VSV specific $K^b$ restricted CTL.
Figure 2C:
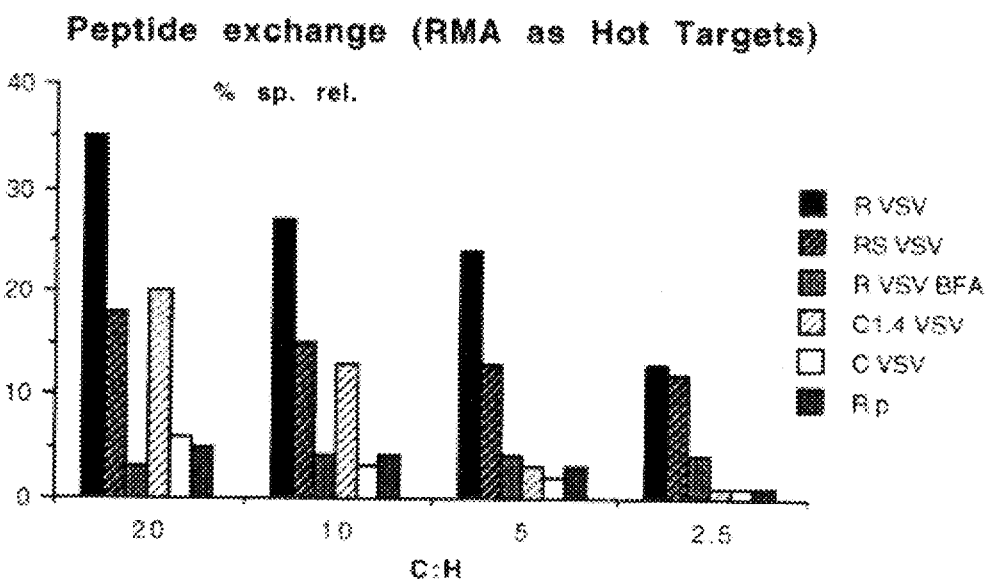
FIG. 2C is a bar graph showing ability of TAP 1 expressing CMT.1-4 cells to generate and transfer peptides to uninfected, chromium laden, target cells.

In FIG. 2B, we show that T1, NIH 3T3 and L cells are not lysed by VSV specific K$^b$ restricted CTL. However, each of these cell types can transfer peptides to RMA cells (FIG. 2A). Accordingly, the wild-type T1 cells, though not recognised by VSV specific CTL are able to transfer a VSV peptide.

Example 3

Role of TAP transporters and MHC class I molecules in peptide transfer

In order to establish the significance of individual components of the antigen processing pathway for peptide transfer, we investigated whether cell variants deficient in one or more elements of this pathway are able to transfer peptide. Human T2 (R. D. Salter and P. Cresswell. EMBO J. 5:943, 1986) and murine CMT.64 (H-2$^b$) cells (Jefferies W. A., et al. *J. Immunol.* 151:2974, 1993 and Gabathuler et al., 1994, J. Exp. Med. 180:1415) do not express either TAP-1 or TAP-2.

The effect of TAP on peptide transfer was investigated as follows. CTL were generated as described in Example 1. Hot targets were RMA cells treated with [$^{51}$]Cr for 2 hours and subsequently washed 3 times. Cold targets serving as peptide donors consisted of RMA, CMT.64+/-IFN-γ(CMT, and CMT.IFN respectively), and CMT.64 cells transfected with the rat TAP 1 and TAP 2 genes (CMT1.2). These cells were treated with VSV (MOI of 2) for 12 to 18 hours and subsequently washed 3 times. Effectors, cold and hot targets were then incubated together in V-bottom 96-well plates for 4 hours, followed by removal of 100 μ of supernatant which was then counted for radioactivity released.

Figure 3A:
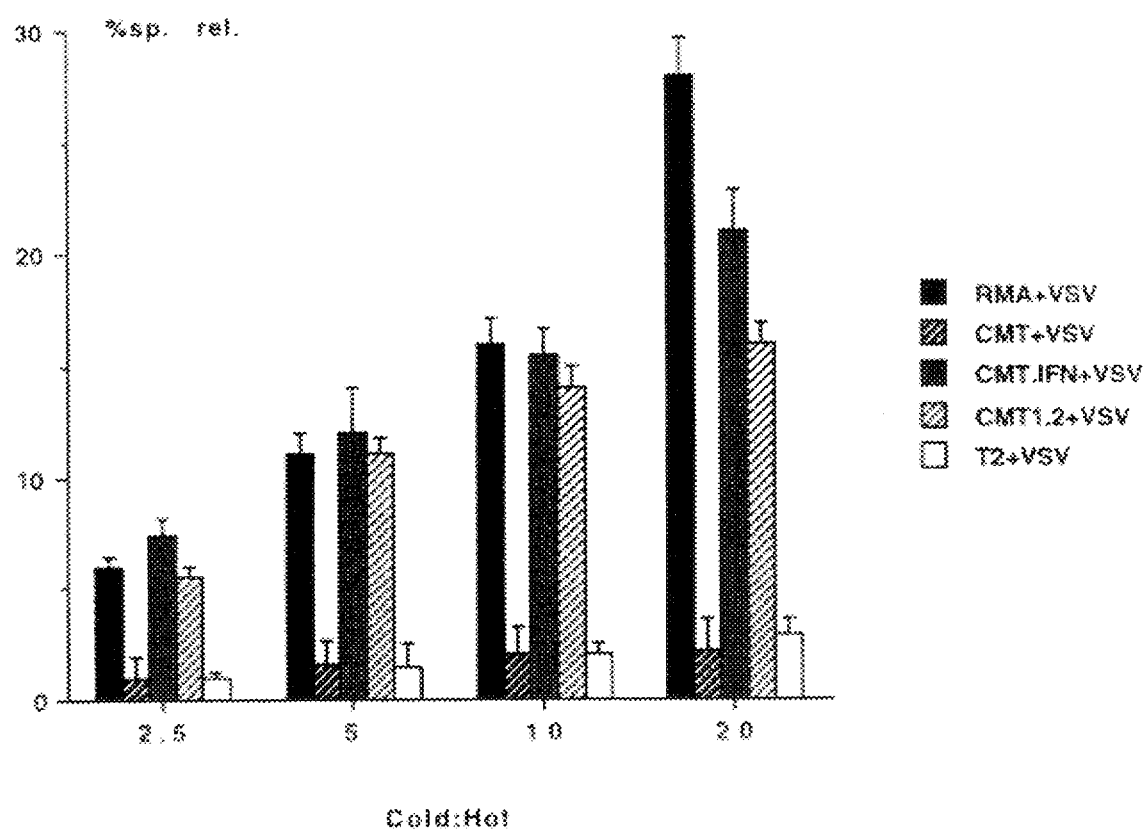
FIG. 3A is a bar graph showing that VSV infected human T2 and mouse CMT.64 cells are not recognized by VSV specific $K^b$ restricted CTL.

Following infection with VSV, we found that neither the T2 or CMT.64 cell lines were recognized by VSV specific K$^b$ restricted CTL (Jefferies W. A., et al. *J. Immunol.* 151:2974, 1993) (data not shown) and were unable to efficiently transfer peptides to the recipient RMA cells as shown in FIG. 3A. As noted above, the wild-type T1 cells, though not recognized by VSV specific CTL (FIG. 2B), are able to transfer a VSV peptide (FIG. 2A). CMT.64 cells induced with IFN-γ to express TAP-1 and -2 were able to transfer peptide(s) (FIG. 3A). Furthermore, CMT.64 transfected with the rat TAP-1 and TAP-2 genes were able to transfer a peptide to RMA cells (FIG. 3A). These data demonstrate that infected cells which lack TAP transporters cannot transfer peptide(s). These results reveal a dependency on the expression of the TAP transporters for the exchange of peptide(s) and suggest that the peptides must be translocated into the ER in order to be transferred.

In order to investigate whether interaction with/and transport by MHC class I molecules is a prerequisite for peptide transfer, we examined whether murine R1.E (H-2$^k$) cells (D. B. Williams, et al. *J. Immunol.* 142:2796, 1989) which lack β2 microglobulin and therefore do not transport MHC class I heavy chain are able to transfer a VSV peptide.

The effect of heavy and light chains on peptide transfer was investigated as follows. CTL were generated as described in Example 1. Hot targets were RMA cells treated with [$^{51}$]Cr for 2 hours and subsequently washed 3 times. Cold targets consisted of R1E cells and their derivatives R1E transfected with K$^b$(R1EKb), and R1E transfected with β2 m and K$^b$(R1EKbb2). Cold targets were treated with or without (R1EKbb2+—) VSV (MOI of 2) for 12 to 18 hours and subsequently washed 3 times. Effectors, cold and hot targets were then incubated together in V-bottom 96-well plates for 4 hours, followed by removal of 100 μl of supernatant which was then counted for radioactivity released. The results are shown in FIG. 3B.

Figure 3B:
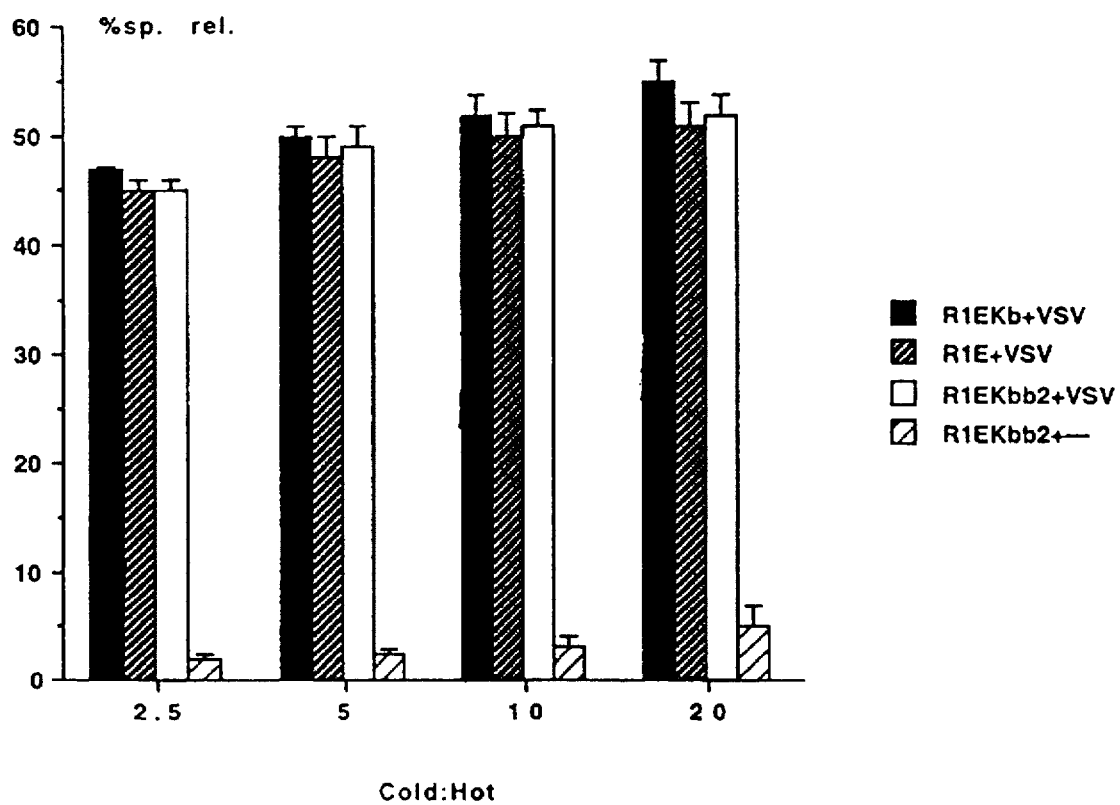
FIG. 3B is a bar graph showing the effect of heavy and light MHC chains on peptide transfer using β2 m deficient R1E cells and R1E cells transfected with $K^b$(R1EKb), and R1E transfected with β2 m and $K^b$(R1EKbb2), with or without VSV treatment.

R1.E cells were able to efficiently transfer peptides to RMA cells as shown in FIG. 3B. The contribution of K$^b$ molecules alone and of K$^b$ and β-2 microglobulin to this peptide transfer was established by examining R1.E cells derivatives transfected with heavy or heavy and light chains. The expression of K$^b$ alone and both K$^b$ and beta-2 microglobulin did not affect the efficiency of peptide transfer of transfected R1.E cells (FIG. 3B). This indicated that peptide binding and transport of MHC class I molecules was not required for transfer of the peptide.

Example 4

Effect of Brefeldin A on Peptide secretion from infected cells

In order to address whether peptides are secreted from infected cells we used brefeldin A, an inhibitor of protein secretion. Brefeldin A was used at concentrations reported previously (Jefferies W. A., et al. *J. Immunol.* 151:2974, 1993, Nuchtern, J. G., et al. *Nature* 339:223, 1989; Yewdell, J. W. and J. R. Bennink. *Nature* 339:223, 1989) which effectively inhibit protein secretion but does not harm cell viability. Brefeldin A treated RMA cells were infected with VSV and examined for their ability to transfer peptide to recipient cells.

The effect of BFA on peptide transfer was investigated as follows. CTL were generated as in Example 1. Hot targets were RMA cells treated with [$^{51}$]Cr for 2 hours and subsequently washed 3 times. Cold RMA cells were treated with RMA.BFA) or without brefeldin A 10 µg/ml (BFA) and/or VSV (MOI of 2) for 12 to 18 hours and subsequently washed 3 times. Effectors, cold and hot targets were then incubated together in V-bottom 96 well plates for 4 hours, followed by removal of 100 µl of supernatant which was then counted for radioactivity released.

Figure 4:
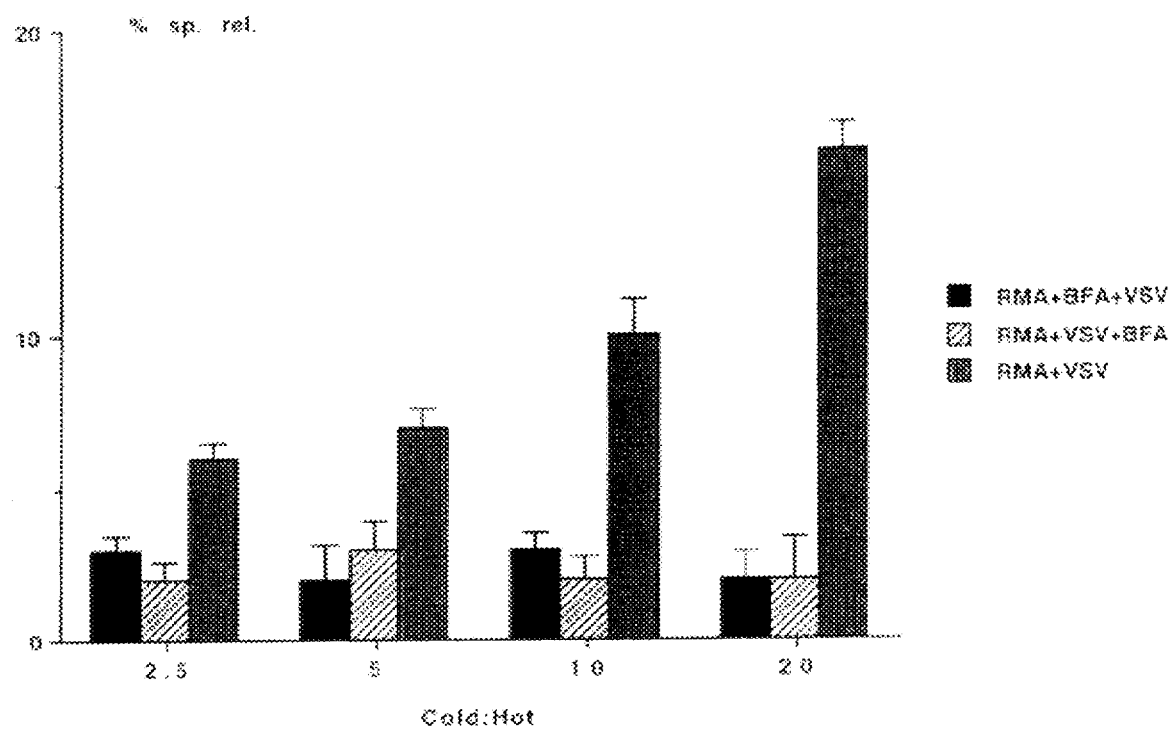
FIG. 4 is a bar graph showing the effect of brefeldin A (BFA) on peptide transfer.

We found that brefeldin A dramatically inhibited peptide transfer as shown in FIG. 4, suggesting that the peptide must be actively transported through the secretory pathway for efficient transfer to take place. This was also confirmed by our observation that growth media from Ltk- cells infected with VSV and collected before virally induced lysis could sensitize uninfected RMA cells for CTL recognition.

Example 5

Supernatants from VSV infected Ltk cells sensitize recipient uninfected RMA cells for VSV specific CTL recognition Cold targets were replaced with supernatant of VSV infected cells in the assay described in Example 1. Supernatant of VSV infected cells was collected 12 hours post infection, before any virally induced lysis, desalted through a G.25 column and lyophilized before reconstitution in 2 ml of medium to achieve a 5× concentration. The supernatant was added to $^{51}$Cr laden RMA cells and the resulting CTL mediated lysis measured. The $[^{51}]$Cr release was measured by an LKB1282CS Compugamma counter and the specific $[^{51}]$Cr release calculated as (experimental-media control)/(total-media control)×100%. The spontaneous release never exceeded 20% of the maximum release (treated with 1.5% Triton X-100).

Figure 5:
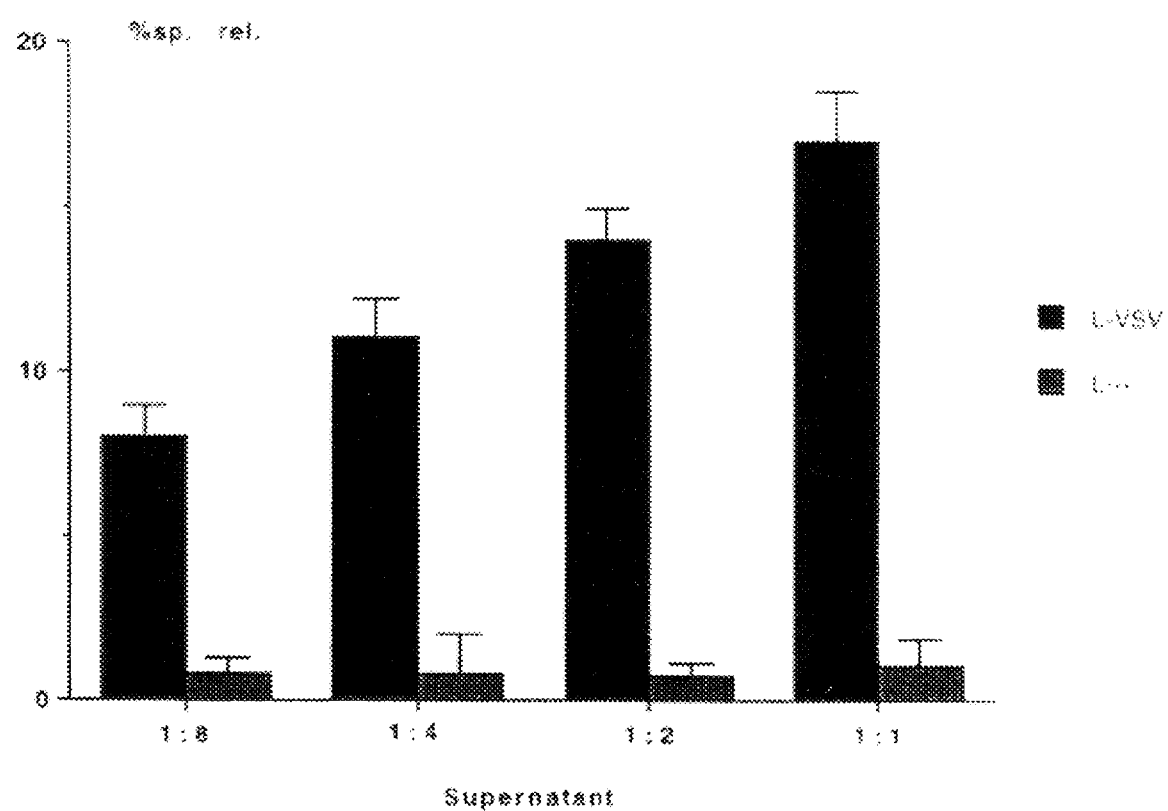
FIG. 5 is a bar graph showing that supernatants from Ltk- cells infected with VSV mediated lysis of RMA cells by VSV specific CTL.
Figure 6:
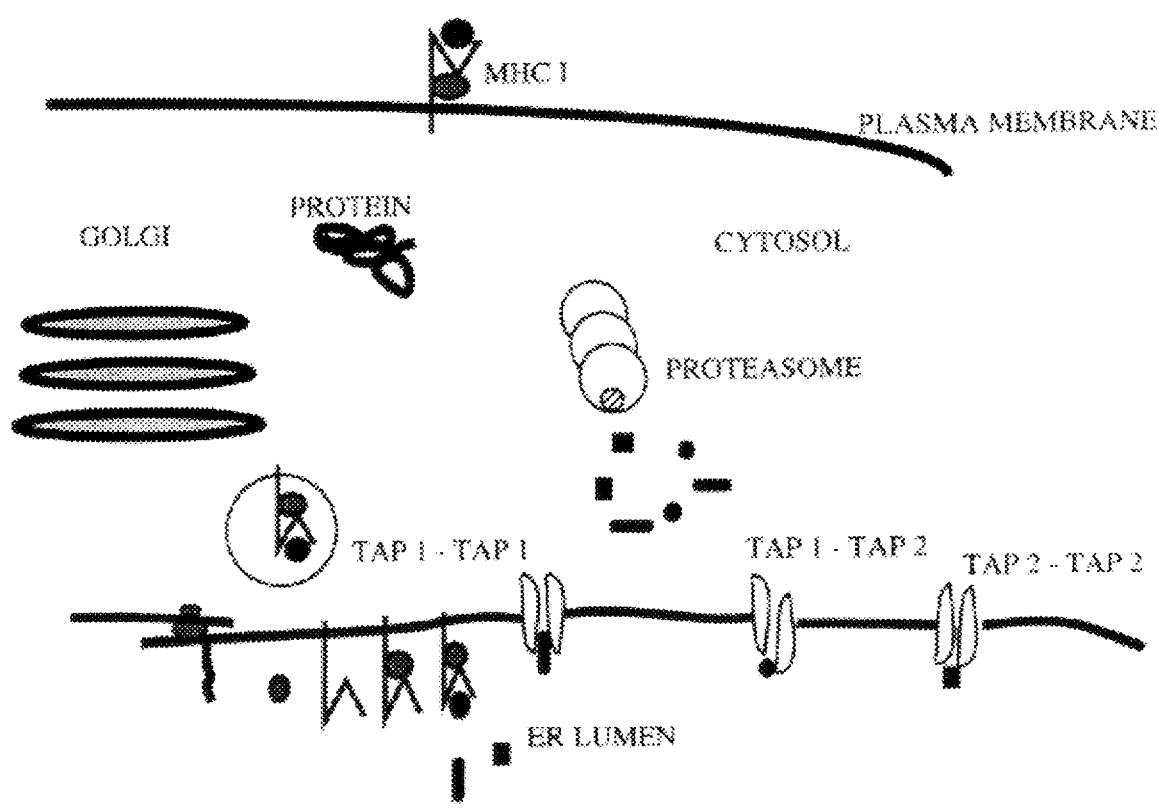
FIG. 6 is a diagram illustrating the surrogate antigen processing of the invention and alternative fate of antigenic peptides within the secretory pathway.

The results are shown in FIG. 5, which shows that the supernatant from the VSV infected cells sensitized uninfected RMA cells for CTL recognition. These results indicate that contact between the donor and recipient cells is not necessary for sensitization of target cells for CTL lysis.

Example 6

Ltk cells transfected with VSV-N transfer peptides to recipient non-transfected RMA cells In order to confirm that the transfer of endogenously processed VSV peptides to recipient target cells for recognition by primed CTL was not an anomaly resulting from the effects of VSV infection of the donor cells, donor cells transfected with VSV-N peptides were prepared. Murine Ltk cells (L cells) were transfected with VSV-N to provide a more controlled and convenient system for the screening of substances that affect the endogenous processing and secretion of antigens.

L cells were transfected as follows. Approximately 1.0 µg of DNA encoding VSV-N and the neophosphotransferase gene was transfected into L cells with lipofectin (2 µl). The transfected cells were selected in geneticin (G418) 1 mg/ml for 4 days and to half the concentration of G418 thereafter. Isolated clones were selected, grown and frozen. The transfected clones were collected after the cells reached confluency. The supernatants were then checked for their ability to sensitize uninfected target cells for recognition and lysis by VSV specific CTL. The following results, expressed in per cent lysis of RMA target cells, were obtained from 7 different clones: L VSV-N 1 44%, L VSV-N 2 49%, L VSV-N 3 38%, L VSV-N 4 35%, L VSV-N 8 37%, L VSV-N 11 35%, and L VSV-N 13 37%.

The transfection of VSV-N was found to be sufficient to sensitize target cells for CTL killing. Transfected L cells were not recognised directly by the VSV specific cells for CTL killing in the C57B1/6 mouse (H-2b), but were able to transfer the VSV-N peptide to target cells expressing the $K^b$ molecule. This confirms that endogenous proteins can produce peptides which are secreted and transferred to target cells.

Example 7

Reactivity of CTL after first stimulation

Figure 7A:
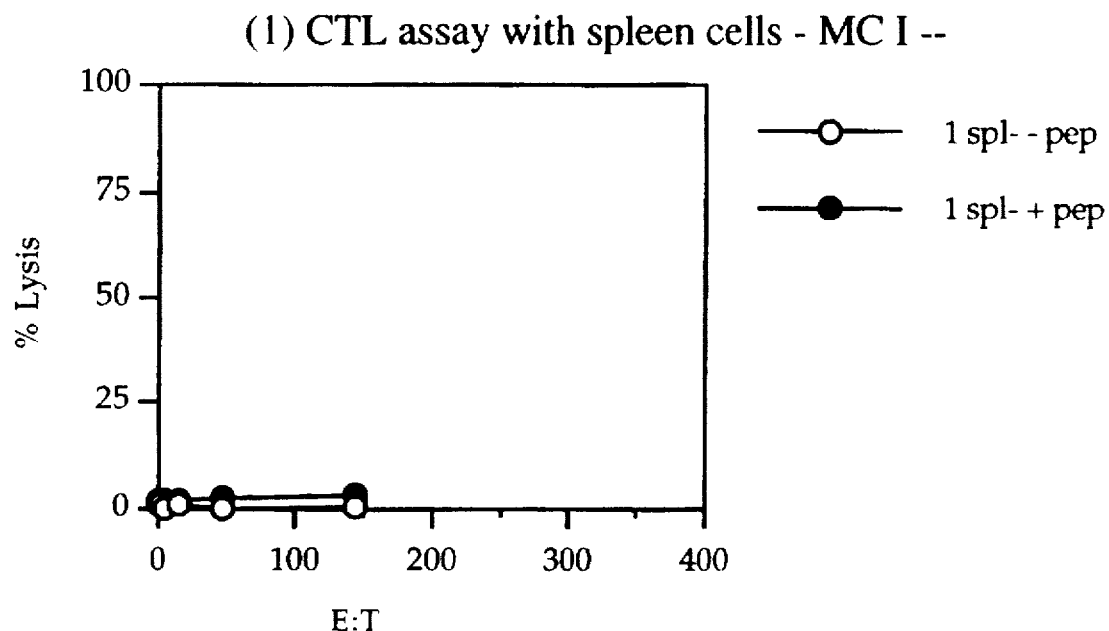
FIG. 7A is a graph showing a CTL control assay from spleen cells not pulsed with VSV-N 52-59 peptide.
Figure 7B:
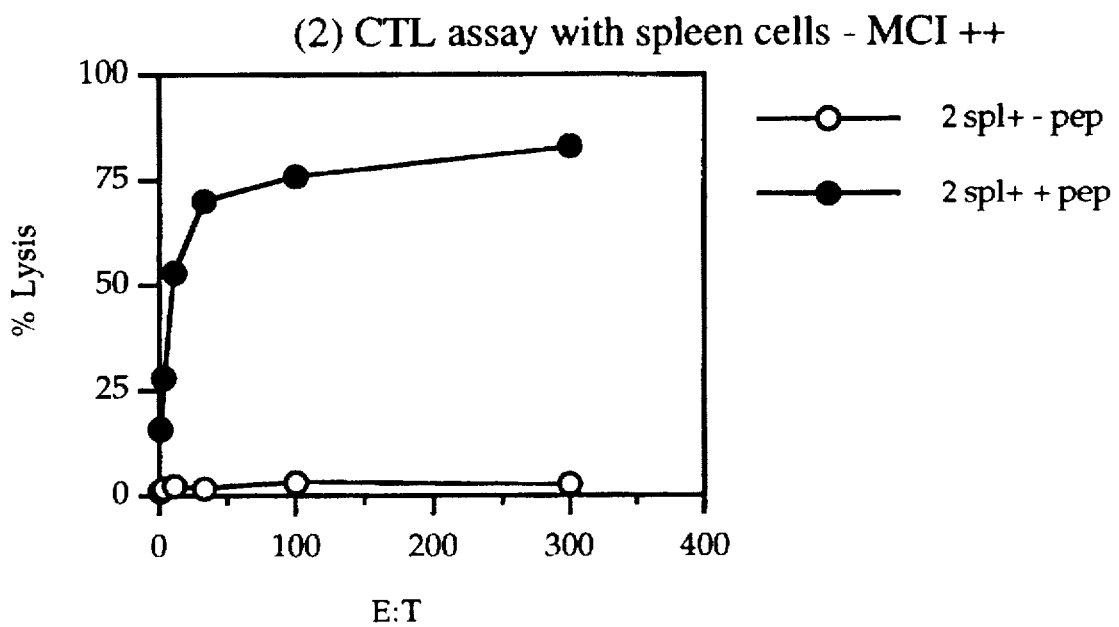
FIG. 7B is a graph showing a CTL assay from spleen cells pulsed with VSV-N 52-59 peptide.
Figure 7C:
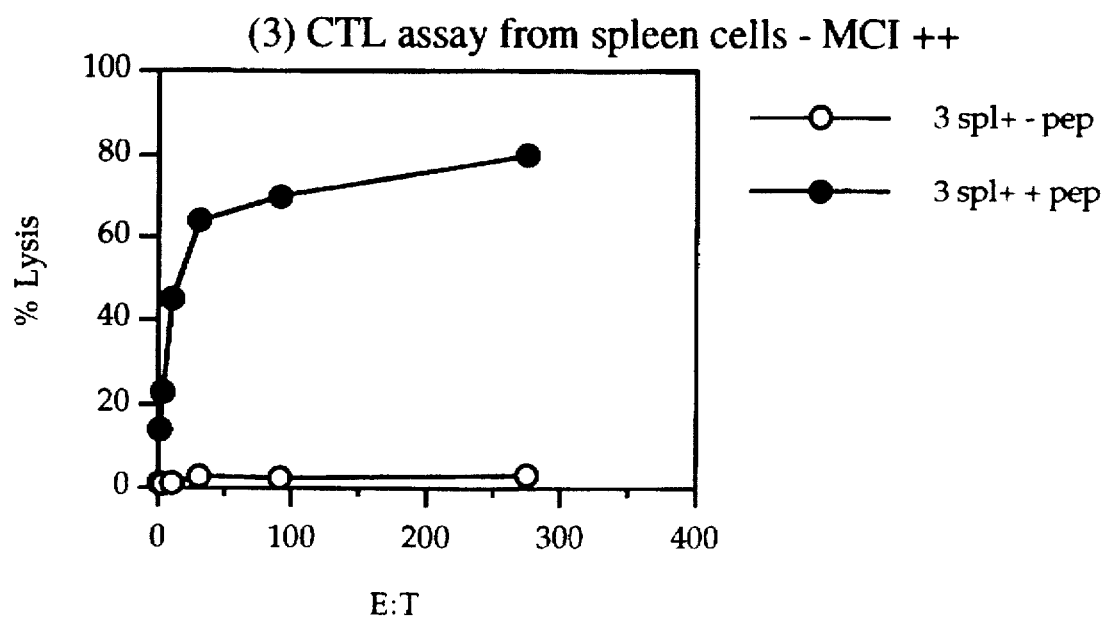
FIG. 7C is a graph showing a CTL assay from spleen cells pulsed with VSV-N 52-59 peptide.
Figure 7D:
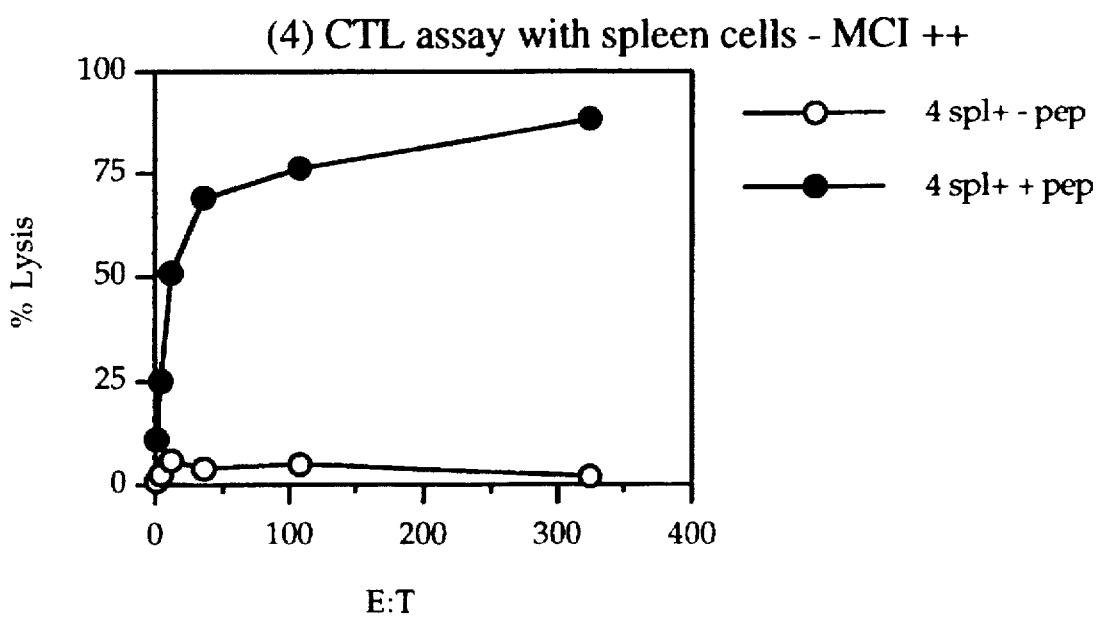
FIG. 7D is a graph showing a CTL assay from spleen cells pulsed with VSV-N 52-59 peptide.

The CTL assay described in example 6 was repeated using spleen cells. Spleen cells from mice (C57 B1/6) infected with VSV were kept in culture for 10 days before restimulation in the presence (spl+) or absence of peptides (spl-). The peptide was VSV-N 52-59 at 1 µM. Restimulation of CTL was done with splenocytes from uninfected C57-B1/6 mice pulsed with 1 µM of the same peptide (spl-+, spl ++) or without peptide (spl—, spl +—) and irradiated for 30 min. prior to addition for restimulation. Targets for the CTL assay are RMA cells pulsed with 1 µM of VSV-N 52-59 peptides and loaded with $[^{51}]$Cr. FIG. 7A, shows that splenocytes must be primed with the peptide and restimulated with peptide pulsed cells in order to recognize efficiently VSV-N 52-59 specific targets. FIGS. 7B, 7C and 7D show that peptides are necessary and must be present for restimulation and in the previous incubation for the generation of specific CTL.

We claim:

1. A method of identifying antigens which are capable of being endogenously processed by a cellular secretory pathway and transferred to bystander target cells for presentation to cytotoxic T lymphocytes, comprising: introducing an antigen into a donor cell lacking in MHC class I molecules; incubating in an in vitro medium the donor cells, primed cytotoxic T lymphocytes having specificity for the antigen, and target cells which express MHC class I molecules and which do not express the antigen and are labelled with a detectable intracellular marker, under suitable conditions such that the donor cells remain intact, and; measuring the amount of detectable marker released into the medium wherein the presence of the detectable marker in the medium indicates that the antigen is capable of being endogenously processed by a cellular secretory pathway and transferred to bystander target cells.

2. A method as claimed in claim 1 wherein the antigen is a viral, bacterial, protozoan, or tumor antigen.

3. A method as claimed in claim 1 wherein the antigen is a self antigen or an alloantigen.

4. A method as claimed in claim 2 wherein the antigen is VSV.

5. A method as claimed in claim 1 wherein the donor cell is transfected with a nucleic acid molecule encoding the antigen.

6. A method as claimed in claim 1 wherein the donor cell is R1.E(H-$2^k$) or a Daudi cell.

7. A method as claimed in claim 1 wherein the detectable marker is [51]chromium.

8. A method as claimed in claim 1 wherein the detectable marker is [51]chromium.

9. A method of assaying if a substance affects processing of an endogenously processed antigen in a cellular secretory pathway, comprising: incubating in an in vitro medium a donor mammalian cell having an antigen capable of being endogenously processed by a secretory pathway of the donor cell, a target cell expressing MHC class I molecules and which do not express the antigen and labelled with a detectable intracellular marker, and primed cytotoxic lymphocytes having specificity for the antigen, in the presence and in the absence of a substance that is suspected of affecting processing of endogenously processed antigen in the cellular secretory pathway, under suitable conditions such that the donor cells remain intact,; measuring the amount of detectable marker released into the medium in the presence and in the absence of the substance, and; comparing the amount of detectable marker released in the presence of the substance with the amount of detectable marker released in the absence of the, substance wherein an increase in the amount of detectable maker in the presence of the substance indicates that the substance stimulates the processing of the antigen and a decrease in the amount of detectable marker in the presence of the substance indicates that the substances inhibits the processing of the antigen.

10. A method as claimed in claim 9 wherein the donor cell lacks MHC class I molecules.

11. A method as claimed in claim 10 wherein the antigen is VSV-N protein and the target cell is RMA.

12. A method of characterizing a tumor or viral antigen capable of being endogenously processed by a cellular secretory pathway comprising obtaining, from a mammal, tumor cells or virally infected cells and primed cytotoxic T lymphocytes having specificity for the tumor or virally infected cells; preparing a cDNA library from the tumor or virally infected cells and expressing the cDNA library in transfected host cells; incubating in a medium, transfected host cells, target cells expressing MHC class I molecules and which do not express the antigen and labelled with a detectable intracellular marker and the primed cytotoxic lymphocytes under suitable conditions such that the donor cells remain intact, and; measuring the amount of the detectable marker released into the medium and identifying those transfected cells capable of causing lysis of the target cells and characterizing the transfected DNA or expression product of the transfected DNA of the identified transfected cells.

13. A method of identifying antigens which are capable of being endogenously processed by a cellular secretory pathway and transferred to bystander target cells for presentation to cytotoxic T lymphocytes, comprising;

(a) introducing an antigen into a donor cell;

(b) incubating in an in vitro medium the donor cells, primed cytotoxic T lymphocytes having specificity for the antigen, and target cells which express MGC class I molecules and which do not express the antigen and are labelled with a detectable intracellular marker, under suitable conditions such that the donor cells remain intact;

(c) measuring the amount of detectable marker released into the medium; and, (d) comparing to an amount of detectable marker released into the medium by controls performed to rule out the possibility that MHC class I bound antigens at the surface of the donor cells are released into the medium to associate with the bystander target cells wherein an increase in the detectable marker in the medium compared to the controls indicates that the antigen is processed by a cellular secretory pathway and transferred to bystander target cells for presentation to cytotoxic T lymphocytes.

14. A method as claimed in claim 13 wherein in step (d) the amount of detectable marker released into the medium is compared to an amount of detectable marker released into the medium by controls having donor cells which have been pulsed with synthetic antigen or donor cells treated with antisense molecules to inhibit expression of MHC class I molecules.

15. A method as claimed in claim 13 wherein the antigen is a viral, bacterial, protozoan, or tumor antigen.

16. A method as claimed in claim 14 wherein the antigen is a viral, bacterial, protozoan, or tumor antigen.

17. A method as claimed in claim 13 wherein the antigen is a self antigen or an alloantigen.

18. A method as claimed in claim 14 wherein the antigen is a self antigen or an alloantigen.

19. A method as claimed in claim 13 wherein the donor cell is transfected with a nucleic acid molecule encoding the antigen.

20. A method as claimed in claim 14 wherein the donor cell is transfected with a nucleic acid molecule encoding the antigen.

21. A method as claimed in claim 13 wherein the detectable marker is [$^{51}$]chromium.

* * * * *